United States Patent
Ban et al.

(10) Patent No.: US 9,835,562 B2
(45) Date of Patent: Dec. 5, 2017

(54) LIQUID HOLDING APPARATUS FOR INSERTION OF A TEST DEVICE INTO A TEST LIQUID

(71) Applicant: Quantimetrix, Redondo Beach, CA (US)

(72) Inventors: Monty Scott Ban, Redondo Beach, CA (US); Brian Robert Fernandez, Los Angeles, CA (US); Andrew Todd Schaeffer, Redondo Beach, CA (US); Mina Ghadessi, Irvine, CA (US)

(73) Assignee: Quantimetrix, Redondo Beach, CA (US)

( * ) Notice: Subject to any disclaimer, the term of this patent is extended or adjusted under 35 U.S.C. 154(b) by 0 days.

(21) Appl. No.: 14/745,657

(22) Filed: Jun. 22, 2015

(65) Prior Publication Data

US 2015/0316484 A1    Nov. 5, 2015

Related U.S. Application Data (63) Continuation of application No. 14/269,568, filed on May 5, 2014, now abandoned.

(51) Int. Cl.
*G01N 21/78* (2006.01)
*B01L 3/00* (2006.01)
(Continued)

(52) U.S. Cl.
CPC .............. *G01N 21/78* (2013.01); *B01L 3/508* (2013.01); *B01L 3/5023* (2013.01); *B32B 37/14* (2013.01);
(Continued)

(58) Field of Classification Search
CPC ........ G01N 21/78; Y10T 436/25; B01L 3/508
See application file for complete search history.

(56) References Cited

U.S. PATENT DOCUMENTS 2,745,545 A    5/1956  Dunning
3,421,615 A    1/1969  Salzer et al.
(Continued)

FOREIGN PATENT DOCUMENTS

| EP | 1063508 A1 | 12/2000 |
|---|---|---|
| GB | 1337809 A | 7/1971 |
| WO | 0029111 A1 | 5/2000 |

OTHER PUBLICATIONS

Krohn, James V. et al., "Optimizing Barrier Performance of Multi-Layer Polyethylene Films," Equistar Chemicals LP, pp. 1-9.
(Continued)

*Primary Examiner* — Sam P Siefke
(74) *Attorney, Agent, or Firm* — Jeffrey G. Sheldon; Cislo & Thomas (57) ABSTRACT

A liquid holding apparatus for insertion of a test device into a test liquid, the liquid holding apparatus having a) a liquid holding device for holding test liquid; and b) test liquid in the liquid holding device. The liquid holding device has a front wall and a rear wall. The upper section of the liquid holding device has an access section where the front wall can be detached from the rear wall to allow access for a test strip test device. At least a portion of the front wall is substantially transparent or translucent. The front wall is attached to the rear wall at the access section by a first lamination and the front wall is attached to the rear wail below the access section by a second lamination. The peel strength of the second lamination is greater than the peel strength of the first lamination.

23 Claims, 9 Drawing Sheets

(51) Int. Cl.
   *B32B 37/14* (2006.01)
   *B32B 38/00* (2006.01)
   *A61B 10/00* (2006.01)

(52) U.S. Cl.
   CPC ............ *B32B 38/00* (2013.01); *A61B 10/007* (2013.01); *B01L 2200/085* (2013.01); *B01L 2300/0825* (2013.01); *B01L 2300/0887* (2013.01); *Y10T 436/25* (2015.01)

(56) References Cited

U.S. PATENT DOCUMENTS

| | | | | |
|---|---|---|---|---|
| 3,454,210 | A | * | 7/1969 | Spiegel ................ B65D 75/30 229/123.1 |
| 3,752,743 | A | | 8/1973 | Henshilwood |
| 3,835,834 | A | | 9/1974 | Bailey et al. |
| 3,913,562 | A | | 10/1975 | Moore et al. |
| 4,116,336 | A | | 9/1978 | Sorensen et al. |
| 4,678,754 | A | | 7/1987 | Hoskins |
| 4,769,261 | A | | 9/1988 | Hazelton et al. |
| 4,880,111 | A | * | 11/1989 | Bagwell ............ B65D 81/3266 206/209.1 |
| 4,923,063 | A | * | 5/1990 | Tararuj ............... B65D 75/5833 206/469 |
| 4,965,047 | A | | 10/1990 | Hammond et al. |
| 5,445,838 | A | | 8/1995 | Lipinski et al. |
| 5,916,815 | A | | 6/1999 | Lappe |
| 6,159,747 | A | | 12/2000 | Harttig et al. |
| 6,287,612 | B1 | | 9/2001 | Mandava et al. |
| 6,475,805 | B1 | * | 11/2002 | Charm ................ G01N 33/537 422/110 |
| 6,712,201 | B1 | * | 3/2004 | Bertram ............... B29C 44/183 206/219 |
| 7,431,882 | B2 | | 10/2008 | Parker |
| 7,530,740 | B2 | | 5/2009 | Geyer |
| 7,749,453 | B2 | | 7/2010 | Rannikko et al. |
| 7,850,923 | B2 | | 12/2010 | Byrd |
| 8,201,689 | B2 | | 6/2012 | Kaern |
| 2001/0012637 | A1 | | 8/2001 | Casterlin et al. |
| 2007/0031653 | A1 | | 2/2007 | Su |
| 2007/0065339 | A1 | | 3/2007 | Huff |
| 2007/0144922 | A1 | * | 6/2007 | Imoarai ................ G01N 33/52 206/204 |
| 2007/0274869 | A1 | | 11/2007 | Rannikko et al. |
| 2012/0070906 | A1 | | 3/2012 | Ban et al. |
| 2012/0208288 | A1 | | 8/2012 | Ban et al. |
| 2015/0314286 | A1 | | 11/2015 | Ban et al. |

OTHER PUBLICATIONS

Finson, E. et al, "Transparent SiO2 Barrier Coatings: Conversion and Production Status," Airco Coating Technology, Concord, CA, pp. 139-143.
Toray Plastics, Product Technical Data Sheet for Barrialox IO11EG Series, TPA Jun. 2007.
Voss, Peter A., Article on Adhesive presented at the Adhesive and Sealant Council's Spring Convention, Mar. 22-25, Orlando, FL, Copyright PRIMEDIA Intertec May 1998.
Dow Chemical, Product Technical Data Sheet on Saranex 553 Coextruded Barrier Film, Jul. 23, 2010.
Dow Chemical, Product Technical Data Sheet on Saranex 450 Coextruded Barrier Film, Jul. 23, 2010.
Dow Chemical, Product Technical Data Sheet on Saranex 451 Coextruded Barrier Film, Jul. 23, 2010.
Continental Steel & Tube Co., Product Information Sheet on Aluminum Sheet and Coil-Series 1100-0.
Popp, Nick, Film Specification for: Film Pouch, Foil, HSVFFS Machine, Sokol and Company, Countryside, IL 2006.
Quantimetrix Corp., Product Information Sheet on "Dropper Urine Dipstick Control".
Quantimetrix Corp., Product Information Sheet on "Dipper Urine Dipstick Control".
Quantimetrix Corp., Product Information Sheet on "Dropper Plus Point-of-Care Urine Dipstick Control".
Quantimetrix Corp., Product Information Sheet on "QuanTscopics Urine Miscroscopics Control".
EP12176204, European Patent Office Extended Search Report dated Jan. 16, 2013.
United States Patent and Trademark Office, Office Action, U.S. Appl. No. 13/239,103, Applicant Name: Monty Scott Ban, dated Feb. 7, 2014.
United States Patent and Trademark Office, Office Action, U.S. Appl. No. 13/239,103, Applicant Name: Monty Scott Ban, dated May 29, 2014.
USPTO, Office Action issued in related U.S. Appl. No. 13/371,716 dated Sep. 19, 2014, 32 pages.
USPTO, Office Action issued in related U.S. Appl. No. 13/239,103 dated Oct. 10, 2014, 22 pages.
USPTO, Office Action issued in related U.S. Appl. No. 14/269,568 dated Nov. 23, 2015, 16 pages.
Personal Excel Spreadsheet: "SSK Pouch Film Savings"—Compilation of various multi-layer film structures from different listed manufacturers, Nick Popp, 2004.
Personal Excel Spreadsheet: "SSK Film Costs 2"—From a compilation of various multi-layer film structures from different listed manufacturers, Nick Popp, 2004.
USPTO, Office Action issued in related Ban et al. U.S. Appl. No. 14/269,568 dated Nov. 18, 2016, 24 pages.

* cited by examiner

LIQUID HOLDING APPARATUS FOR INSERTION OF A TEST DEVICE INTO A TEST LIQUID

CROSS-REFERENCE TO RELATED APPLICATION

This application is a continuation-in-part of U.S. patent application Ser. No. 14/269,568 titled "LIQUID HOLDING APPARATUS FOR INSERTION OF A TEST DEVICE INTO A TEST LIQUID," filed May 5, 2014, the contents of which are incorporated in this disclosure by reference in their entirety.

BACKGROUND OF THE INVENTION

This invention relates to small, portable liquid holding apparatuses used for the insertion of a test device into a test liquid. Small portable liquid holding apparatuses are used for a variety of applications.

In typical applications, liquid holding apparatuses are used in urinalysis (also called a routine urine test) to check for abnormalities in urine. Urine is liquid waste that is made by the kidney's and stored in the bladder until it is eliminated by the body through urination. A number of diseases and conditions can result in abnormalities in the urine. These abnormalities may be detected through physical, chemical, and microscopic examination. Urinalysis may be performed as part of a regular physical examination to screen for early signs of disease.

Urinalysis was the very first laboratory test developed—the value of urine testing to diagnose medical conditions was established over 6000 years ago. There is evidence of visual testing of urine in the earliest civilizations. As advances in medicine are proved visual testing to be unreliable, chemical evaluation of the urine replaced this method as a more accurate means of diagnosis.

Further understanding of the structure of the body (anatomy) and of the physical and chemical processes involved in organ function (physiology), as well as the invention and development of the microscope, led to additional advances in urine testing as a diagnostic tool. Urinalysis was first introduced as part of the routine physical examination in 1827, and this test remains a valuable method of diagnosis.

Dipstick tests involve placing papers that contain small pads of chemicals into the urine sample. These papers, referred to as urine dipsticks and urine reagent strips, change color when exposed to various substances in the urine. This type of urine testing can result in false-positive or false-negative results. Therefore, most laboratories use urine dipstick controls to determine whether the dipsticks are performing properly.

Urine dipstick controls mimic patient samples and are fortified to target levels with compounds that produce the desired reaction when tested by the dipsticks. This is an accurate means of determining the performance of the dipsticks to insure accurate results from patient specimens. If a dipstick is found to provide inaccurate results, the dipsticks are discarded and a new package is tested. If the dipsticks in the new package perform within specifications, then the dipsticks are used to test actual patient samples. Medical technologists run controls on a daily basis in order to be compliant with state and federal regulations governing quality control in the clinical setting. The controls can be urine or synthetic urine.

Hospital and reference laboratories have used controls for urinalysis dipstick testing for many years. These laboratories typically have large refrigeration units located in close proximity to the actual location where testing is performed. This means that a medical technologist working in the lab would simply remove the control material from the refrigerator as needed. All liquid, ready-to-use, quality control material requires refrigeration in order to achieve maximum stability.

In recent years, a trend towards point-of-care urine dipstick testing has occurred. This means that more testing is being performed by nurses at the point-of-care. Nurses have different needs from medical technologists. One of the most important needs is that they may not have refrigeration suitable to store in-vitro diagnostic products, such as urine dipstick controls. The refrigeration that is available to them is usually dedicated for the storage of items such as medication and food. Therefore, nurses require controls that feature extended room temperature stability. Additionally, nurses require controls that are portable so that they can easily be transported to the point-of-care (bedside, nurses' station, etc.).

There is a need for a liquid holding apparatus which is easier to use, less expensive to manufacture and less prone to spilling accidents than liquid holding apparatuses of the prior art.

SUMMARY

The invention satisfies this need. In a first aspect, the invention is a liquid holding apparatus for insertion of a test device into a test liquid, the liquid holding apparatus comprising: a) a liquid holding device for holding the test liquid, the liquid holding device having an upper section and a lower section, the liquid holding device comprising a front wall with a forward facing surface and a rear wall with a rearward facing surface, the upper section of the liquid holding device having an access section where the front wall can be detached from the rear wall to allow access for the test strip test device, at least a portion of the front wall being substantially transparent or translucent to allow visual inspection of a test device inserted into the liquid holding device; and b) test liquid in the liquid holding device. In this aspect of the invention, the front wall is attached to the rear wall at the access section by a first lamination and the front wall is attached to the rear wall below the access section by a second lamination. The peel strength of the second lamination is greater than the peel strength of the first lamination.

In a second aspect, the invention is a method of using the control device described above comprising the steps of: a) holding the apparatus of claim 1 by the upper section of the liquid holding device above the access section; opening the access opening to the second lamination; and inserting the test strip test device into the test liquid.

In a third aspect, the invention is a method of forming the control device described above comprising the steps of: a) laminating the front wall to the rear wall except at the access section to form the liquid holding device; b) placing test liquid into the liquid holding device through the access section; c) laminating the front wall to the rear wall at the access section; and d) laminating the front wall to the rear wall below the access section with sufficient pressure, temperature and dwell that the seal formed thereby is stronger than the seal at the access section.

DRAWINGS

These and other features, aspects, and advantages of the present invention will become better understood with reference to the following description, appended claims, and accompanying drawings where:

DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers, ingredients or steps.

The Invention

In a first aspect, the invention is a liquid holding apparatus 10 for insertion of a test device 12 into a test liquid 14. The liquid holding apparatus 10 comprises a liquid holding device 16 and test liquid 14 within the liquid holding device 16.

Figure 1:
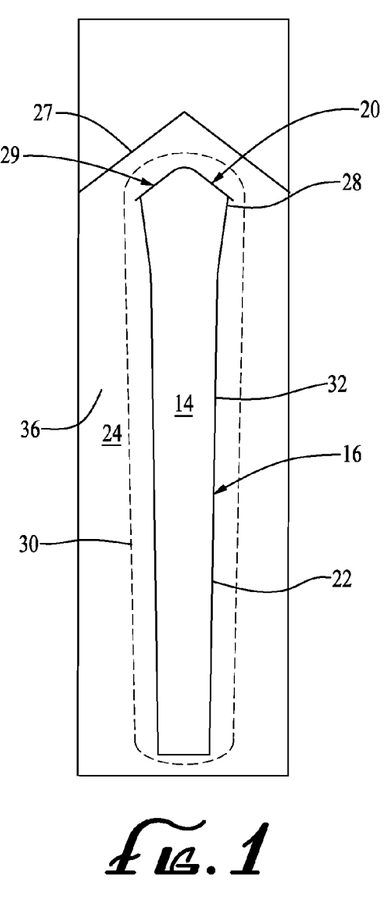
FIG. 1 is a front plan view of a liquid holding device usable in invention.
Figure 2:
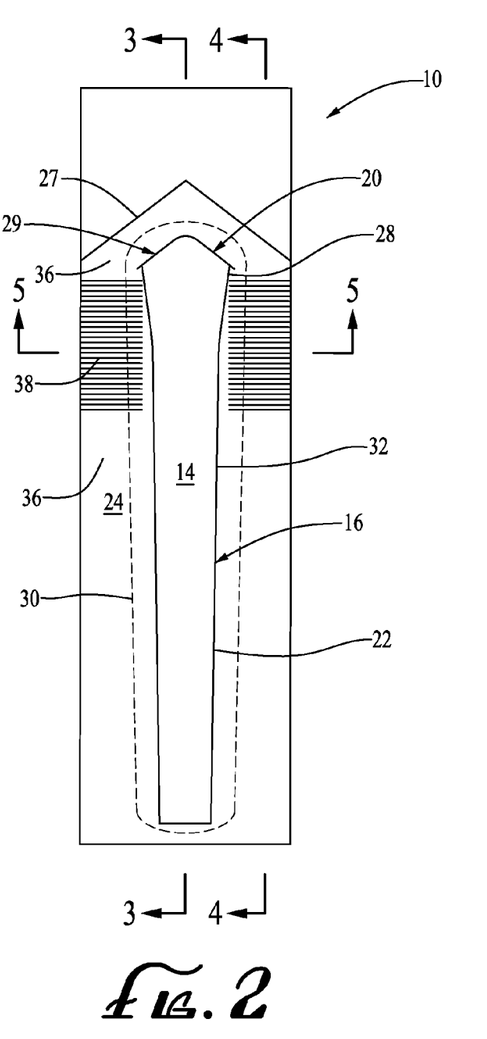
FIG. 2 is a front plan view of a first liquid holding apparatus having features of the present invention.
Figure 3:
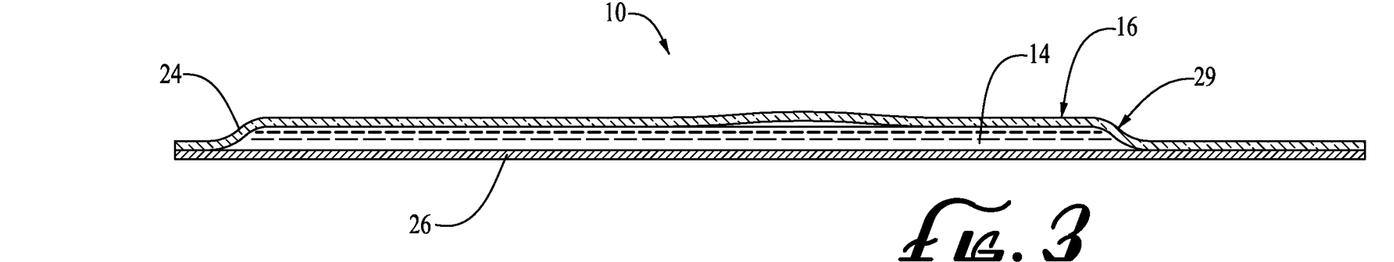
FIG. 3 is a cross-sectional view of the liquid holding apparatus illustrated in FIG. 2, taken along line 3-3.
Figures 4, 5:
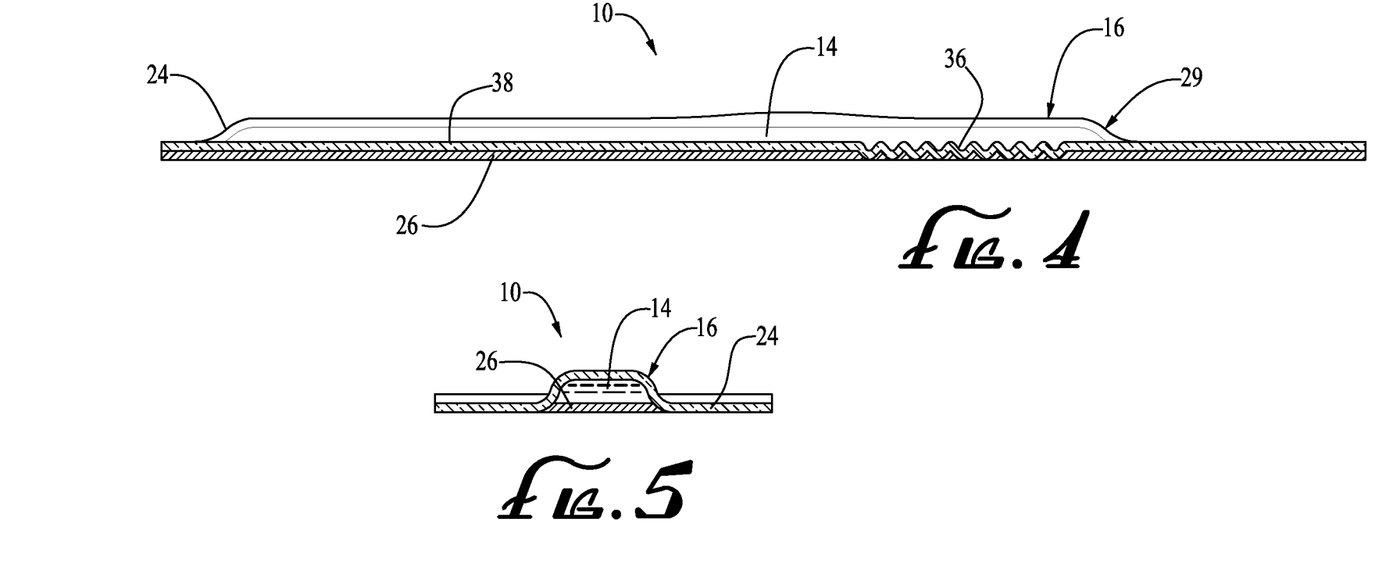
FIG. 4 is a cross-sectional view of the liquid holding apparatus illustrated in FIG. 2, taken along line 4-4.
FIG. 5 is a cross-sectional view of the liquid holding apparatus illustrated in FIG. 2, taken along line 5-5.
Figure 6:
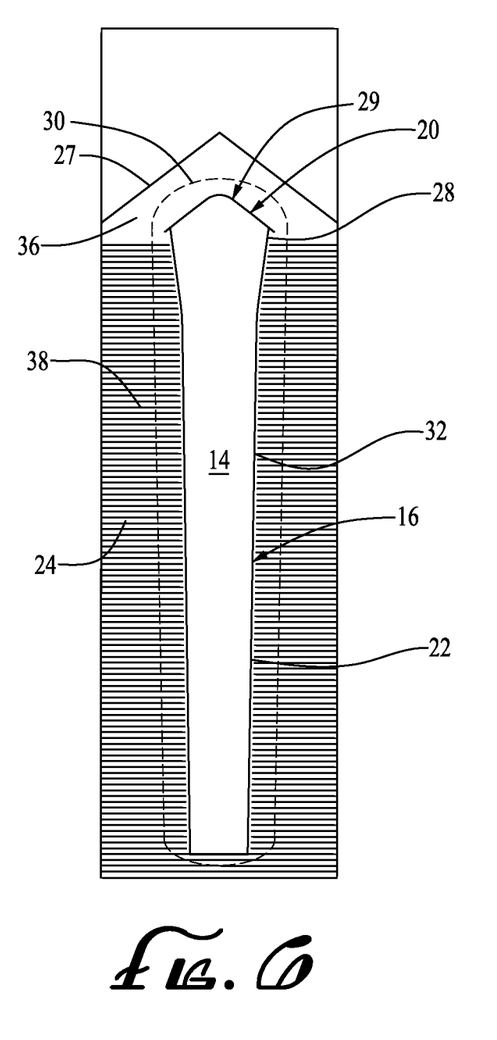
FIG. 6 is a front plan view of a second liquid holding apparatus having features of the present invention.
Figure 7:
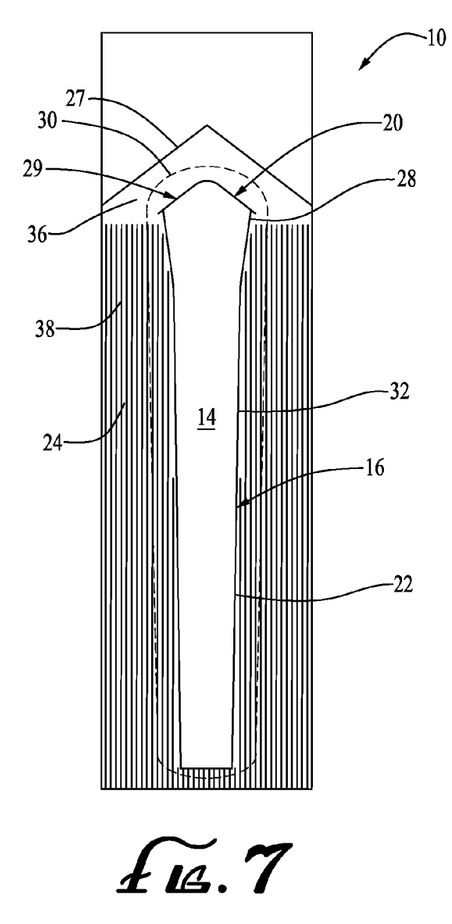
FIG. 7 is a front plan view of a third liquid holding apparatus having features of the present invention.
Figure 8:
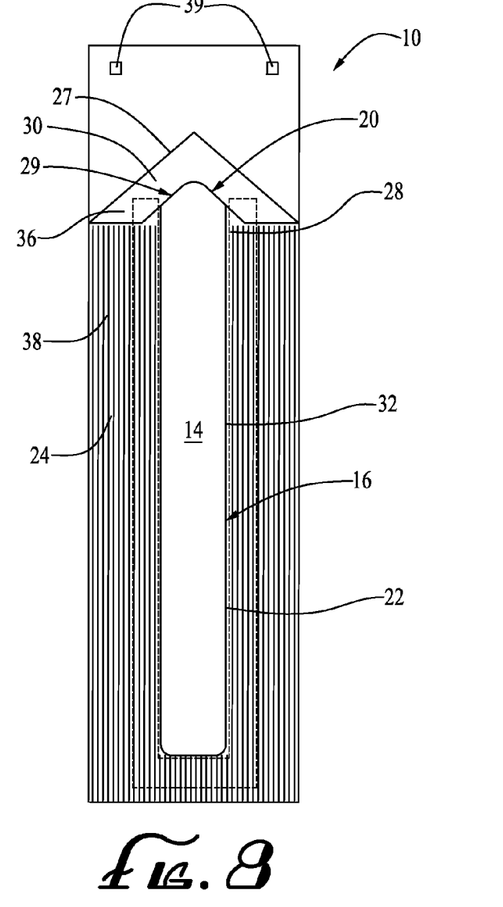
FIG. 8 is a front plan view of a fourth liquid holding apparatus having features of the present invention.
Figure 14:
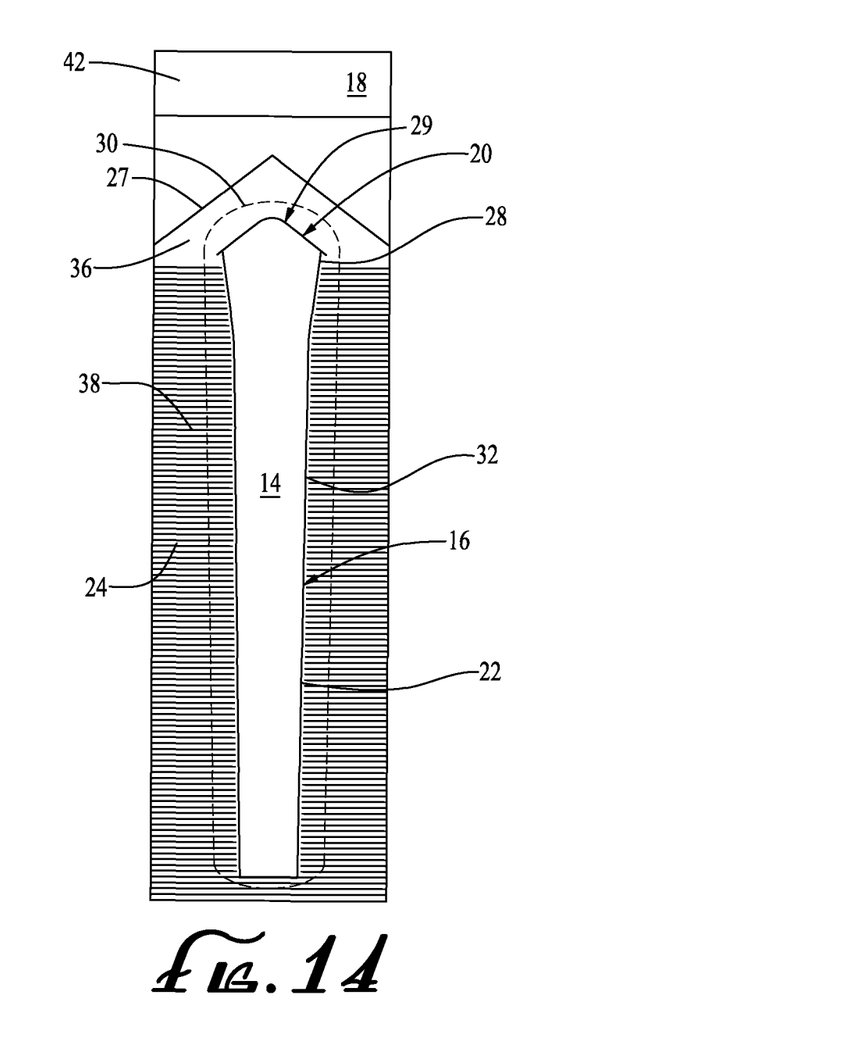
FIG. 14 is a front plan view of a sixth liquid holding apparatus having features of the present invention.
Figure 15:
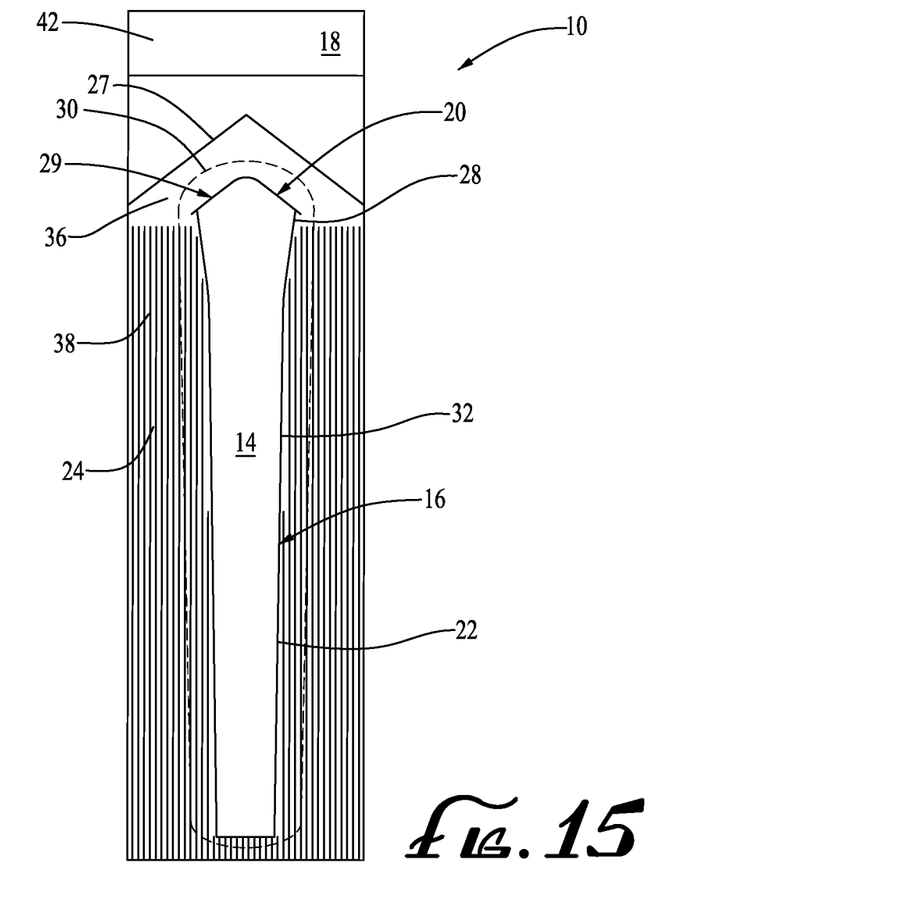
FIG. 15 is a front plan view of a seventh liquid holding apparatus having features of the present invention.
Figure 16:
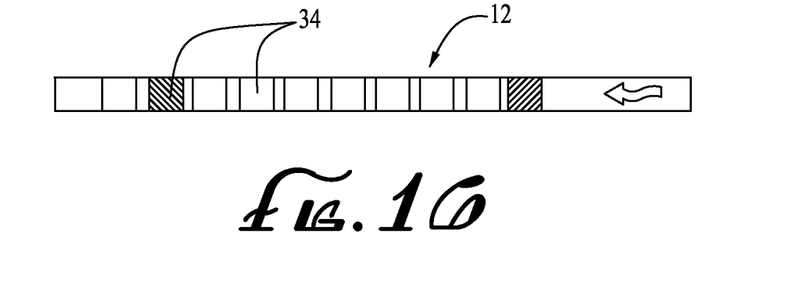
FIG. 16 is a front plan view of a test device which insertable into the liquid holding apparatus of the invention.

FIG. 1 illustrates one embodiment of the liquid holding device 16. FIGS. 2-5 illustrate a first embodiment of the liquid holding apparatus 10. FIG. 6 illustrates a second embodiment of the liquid holding apparatus 10. FIG. 7 illustrates a third embodiment of the liquid holding apparatus 10. FIG. 8 illustrates a fourth embodiment of the liquid holding apparatus 10. FIGS. 10-13 illustrate a fifth embodiment of the liquid holding apparatus 10. FIG. 14 illustrates a sixth embodiment of the liquid holding apparatus 10. FIG. 15 illustrates a seventh embodiment of the liquid holding apparatus 10. FIG. 16 illustrates a test device 12 which can be inserted into the liquid apparatus 10. As shown in FIGS. 1-15, test device 12 is not in the apparatus 10.

The liquid holding device 16 has an upper section 20 and a lower section 22. The liquid holding device 16 also comprises a front wall 24 with a forward facing surface and a rear wall 26 with a rearward facing surface.

The upper section 20 of the liquid holding device 16 has an access section 28 where the front wall 24 can be detached from the rear wall 26 to provide an access opening 29 for allowing access for the test strip test device 12.

At least a portion of the front wall 24 is substantially transparent or translucent. Such substantially transparent or translucent portion is sufficient to allow visual inspection of a test device 12 inserted into the liquid holding device 16.

The liquid holding device 16 has a periphery 30 wherein the front wall 24 and the rear wall 26 are sealed together at the periphery 30.

When the liquid holding apparatus 10 is used in urinalysis, the liquid holding device 16 is sufficiently long that a test device 12 (which is typically about 146 mm long, 5 mm wide and 1 mm thick—and having active portions 34, with the portion of the urine reagent strip having the active portions 34 being about 81 mm long) can be dipped in the liquid holding device 16 with all of the active portions 34 in contact with test liquid. Optionally, the liquid holding device 16 is at least 90 mm in length from the access section 28 to the bottom of the liquid holding device 16.

The liquid holding device 16 is preferably sufficiently long that all active portions 34 of the test device 12 can be immersed in the test liquid 14, and wherein the amount of test liquid 14 in the liquid holding device 16 is sufficiently small that no test liquid 14 flows out of the liquid holding device 16 when the test device 12 is inserted into the liquid holding device 16 a sufficient distance that all active portions 34 are in contact with the test liquid 14.

The volume of test liquid 14 in the liquid holding device 16 is sufficiently small that a test device 12 can be dipped therein without any test liquid 14 leaking out of the liquid holding device 16. Optionally, the liquid holding device 16 contains test liquid 14 in an amount of no more than about 80% the total capacity of the liquid holding device 16. A minimum for typical urine test strip applications is 0.4 ml to a maximum of 5 ml. Fill volume and liquid holding device 16 geometry may vary depending on the application.

The upper section 20 of the liquid holding device 16 has an access section 28 where the front wall 24 can be detachable from the rear wall 26 to provide an access opening 29 for allowing access for a test device 12.

The front wall 24 is typically attached to the rear wall 26 at the access section 28 by a first lamination 36, and the front wall 24 is attached to the rear wall 26 below the access section 28 by a second lamination 38. In the embodiments illustrated in FIGS. 2-6, the second lamination 38 is made in such a way that striations of the second lamination 38 are disposed perpendicular to the longitudinal axis of the liquid holding device 16. In the embodiment illustrated in FIGS. 2-5, the second lamination 38 is made to only a portion of the liquid holding device 16 below the access section 28.

In the embodiment illustrated in FIG. 6, the second lamination 38 is made essentially to the entirety of the liquid holding device 16 below the access section 28.

In the embodiment illustrated in FIG. 7, the second lamination 38 is also made essentially to the entirety of the liquid holding device 16 below the access section 28, but in such a way that striations of the second lamination 38 are disposed parallel to the longitudinal axis of the liquid holding device 16.

FIG. 8 is an alternative version of the embodiment illustrated in FIG. 7. As in the embodiment illustrated in FIG. 7, the second lamination 38 in the embodiment illustrated in FIG. 8 is made essentially to the entirety of the liquid holding device 16 below the access section 28, but in such a way that striations of the second lamination 38 are disposed parallel to the longitudinal axis of the liquid holding device 16. In the embodiment illustrated in FIG. 8, however, the upper section 20 of the liquid holding device 16 does not flare outwardly at the upper end, but instead forms a parallel channel through its entire length. Also, the angle of a chevron-shaped weld 27 which comprises a portion of the first lamination 36 has a slightly taller pitch than in the embodiment illustrated in FIG. 7. Lastly, one or more spot welds or island welds 39 are made in the flap section for aesthetics to maintain the, front wall 24 and the rear wall 26 in contiguous relationship.

In the invention, the peel strength of the second lamination 38 is greater than the peel strength of the first lamination 36. By "peel strength" it is meant a material's ability to resist forces that can pull it apart by separating a flexible surface from a more rigid surface. Peel strength is the measure of the average force to part two bonded materials. Peel strength is calculated during a peel test at a constant speed rate by divided the average force required during the test by the unit width of the bonded samples. Depending on materials, norms, products, the tests can be done with different angles. 90° and 180° are commonly used.

Preferably, the first lamination 36 is peelable by finger strength but sufficient to hold liquid and exclude atmospheric gases. The second lamination 38 is not readily peelable by finger strength.

Figure 9A:
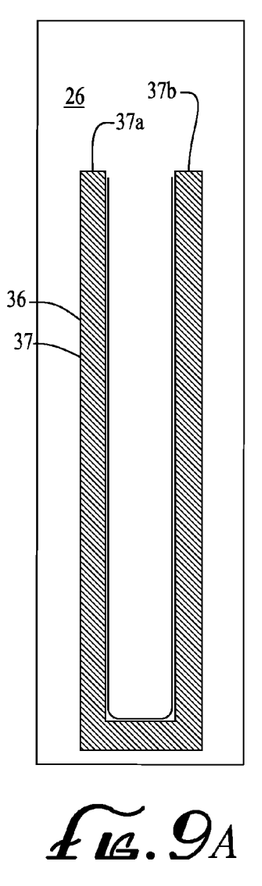
FIG. 9A is a front plan view illustrating a first step in the manufacture of the embodiment illustrated in FIG. 8.
Figure 9B:
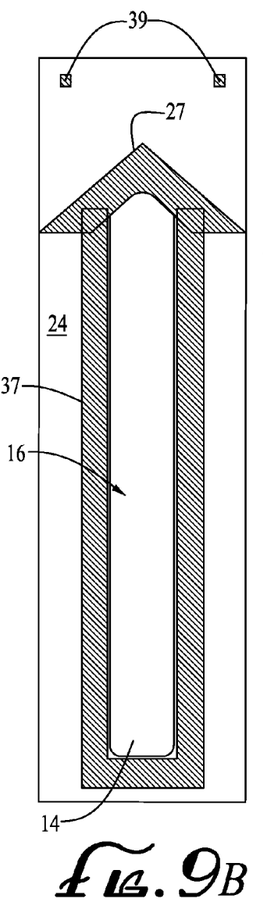
FIG. 9B is a front plan view illustrating a second step in the manufacture of the embodiment illustrated in FIG. 8.
Figure 9C:
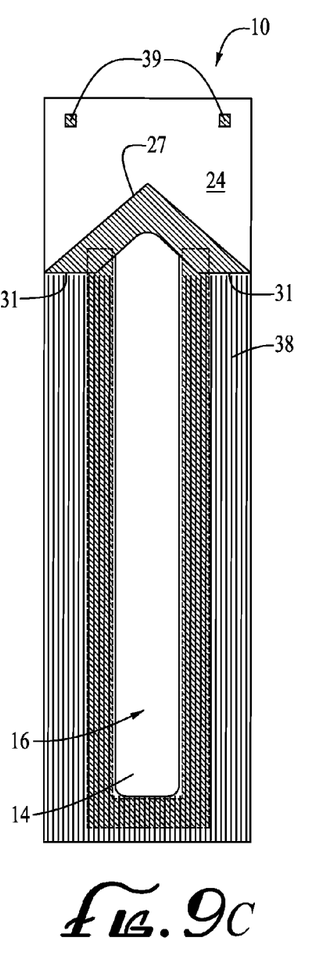
FIG. 9C is a front plan view illustrating a third step in the manufacture of the embodiment illustrated in FIG. 8.
Figure 10:
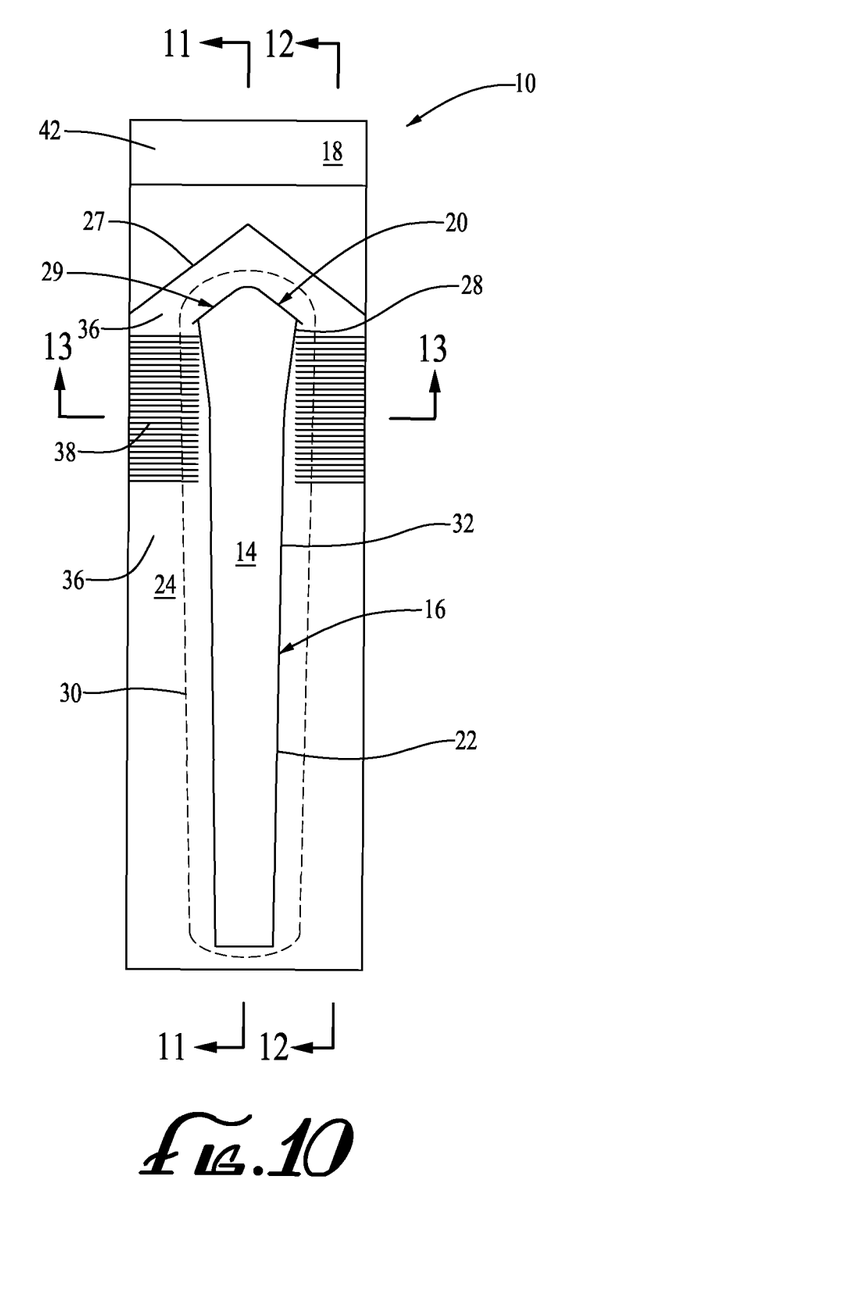
FIG. 10 is a front plan view of a fifth liquid holding apparatus having features of the present invention.
Figure 11:
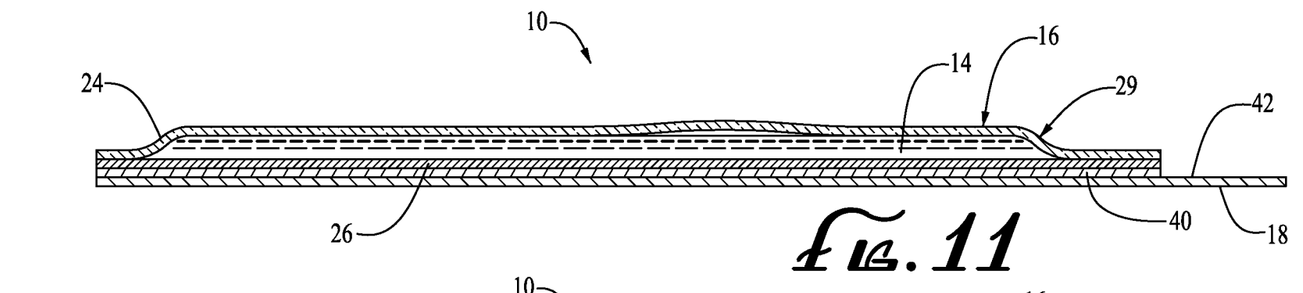
FIG. 11 is a cross-sectional view of the liquid holding apparatus illustrated in FIG. 10, taken along line 11-11.
Figure 12:
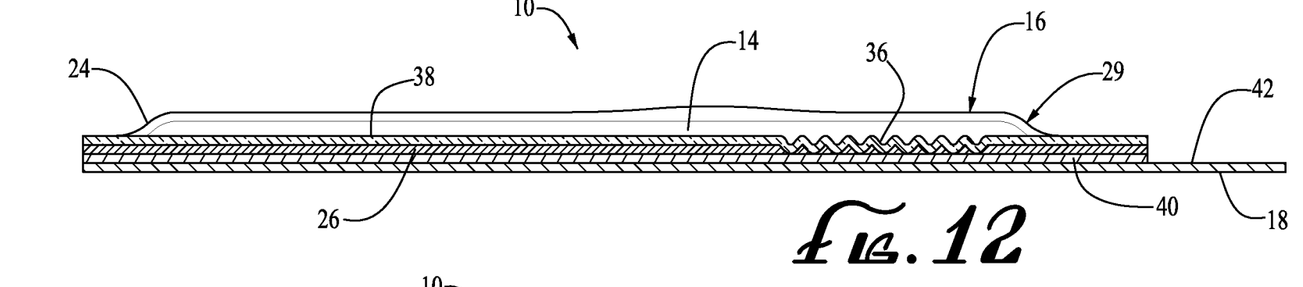
FIG. 12 is a cross-sectional view of the liquid holding apparatus illustrated in FIG. 10, taken along line 12-12.
Figure 13:
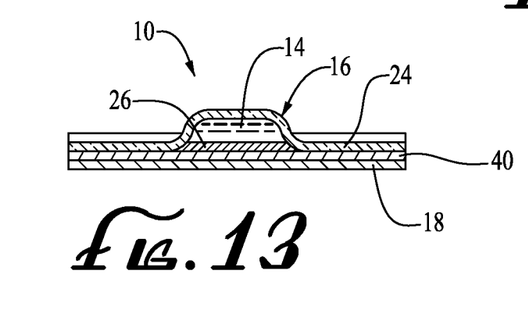
FIG. 13 is a cross-sectional view of the liquid holding apparatus illustrated in FIG. 10, taken along line 13-13.

FIGS. 9A-9C illustrate how the embodiment of FIG. 8 can be manufactured. FIG. 9A depicts a first stage of the manufacturing process wherein the liquid holding device 16 is created, typically using a forming mandrel that provides the third-dimension in the liquid holding device 16. The first lamination 36 of the front wall 24 to the rear wall 26 is provided in part by a first weld 37, which can be formed by a flat seal die heated to approximately 235° F. The first lamination 36 is "peelable" in that it is peelable by finger strength. The first lamination 36 is sufficient to retain test liquid 14 between the front wall 24 and the rear wall 26 without leaking. In the embodiment illustrated in FIGS. 9A-9C, the first weld 37 is substantially U-shaped, having a left edge 37a and a right edge 37b. The left edge 37a and the right edge 37b are typically in parallel to help preserve the third dimension of the liquid holding device 16 throughout the entire length of the liquid holding device 16. After the front wall 24 is attached to the rear wall 26 by the first weld 37, for example about one second thereafter, a filling needle injects test liquid 14 into the enclosed space formed by the first weld 37. Typically, the filling needle is fitted inside of the forming mandrel.

FIG. 9B depicts a second stage of the manufacturing process wherein the first lamination 36 is completed with the chevron-shaped weld 27—effectively enclosing the test liquid 14 within the liquid holding device 16. The chevron-shaped weld 27 is typically created by use of the bottom section of the same seal die that previously created the liquid holding device 16 per FIG. 9A.

The one or more spot welds 39 are also made in this second stage near the top corners of the liquid holding device 16. After this second manufacturing stage, a fully formed three-dimensional filled liquid holding device 16 that is provided, wherein the front wall 24 is "peelable" from the rear wall 26.

FIG. 9C depicts a third stage of the manufacturing process. The second lamination 38 of the front wall 24 to the rear wall 26 is provided over the first lamination 36 with vertical striations—a vertical ribbed weld pattern—around the entire liquid holding device 16 beneath the chevron-shaped weld 27. Typically, this is accomplished using a second seal die, heated to a temperature greater than the temperature of the first die (used in the first stage of the manufacturing process). For example, where the temperature of the first die is about 225° F.-245° F., the temperature of the second die is about 245° F.-265° F. The increased temperature of the second die and the ribbing feature make the second lamination 38 not readily peelable by finger strength (i.e., the second lamination 38 is "permanently sealed").

The output of the third stage is the finished liquid holding device 16 with three general sections: The "peelable" upper section 20 and the "permanently sealed" lower section 22. In the embodiment illustrated in the drawings, the upper section 20 and the lower section 22 meet at along a "stop-peel" line 31.

The ribbed weld pattern also serves to significantly increase the overall stiffness of the liquid holding device 16. Stiffness is the rigidity of an object—the extent to which it resists deformation in response to an applied force. The stiffness, k, of a body is a measure of the resistance offered by an elastic body to deformation. For an elastic body with a single degree of freedom (for example, stretching or compression of a rod), the stiffness is defined as $k=F/\delta$ where, F is the force applied on the body, $\delta$ is the displacement produced by the force along the same degree of freedom.

Stiffness of devices, such as the liquid holding apparatus 10 and the liquid holding device 16, is typically measured on of several stiffness measuring apparatuses known in the industry. One set of such measuring apparatuses is manufactured by Gurley Precision Instruments of Troy, N.Y. Another set of such measuring apparatuses is manufactured by Taber Industries of North Tonawanda, N.Y. The Gurley measuring apparatuses define stiffness in terms of "Gurley units" which are specifically referenced in Test Method T 543 om-00 of TAPPI (originally formed as the "Technical Association of the Pulp and Paper Industry"). TAPPI Test Method T 543 om-00 has been adopted by the Tag and Label Manufacturers Institute. Inc. (TLMI). The Taber measuring apparatuses define stiffness in terms of "Taber Stiffness Units" (often abbreviated as "TSU"). The units of both Gurley units and Taber Stiffness Units are gram-centimeters. Gurley units are known in the industry to be convertible to Taber Stiffness Units by the formula:

$$\text{Taber Stiffness Units} = 0.01419 \text{ (Gurley units)} - 0.935.$$

In the discussion below, stiffness is expressed in Taber Stiffness Units.

Stiffness can be measured by several different measuring apparatuses, including the Taber V-5 Stiffness Tester. The Taber V-5 Stiffness Tester is a bi-directional pendulum weighing system. Stiffness is measured after a deflection of 15°.

Using such measuring apparatus, stiffness can be recorded when an opaque line on the pendulum point remains aligned with a 15° deflection line on a motor driven disc for a period of at least one minute. This takes into account the tendency of many materials to exhibit "elastic fatigue" and subsequent loss of stiffness due to "creeping" of the specimen structure.

Stiffness measured with a Taber V-5 Stiffness Tester or similar device measures stiffness in terms of Taber Stiffness Units. The apparatus is calibrated such that measured stiffness in Taber Stiffness Units reflects the bending moment of ⅕ of a gram applied to a 1½" wide specimen at a 5 centimeter test length, flexing it to an angle of 15°, such that:

$$E=(0.006832\times(1/(w\times d3\times o))\times(\text{Taber Stiffness Units})$$

where,

E=stiffness in flexure in pounds per square inch
w=specimen width in inches;
d=specimen thickness in inches; and
o=deflection of specimen converted to radians (i.e., 15°=0.2618 radians, 7.5°=0.1309 radians)

The overall stiffness of the liquid holding apparatus 10 and the liquid holding device 16 is an important feature as it allows for the easy insertion and removal of a urine dipstick. Preferably, the ribbed weld pattern provides the liquid holding device 16 with an overall stiffness of at least about 15 TSU. In a typical embodiment, the ribbed weld pattern provides the liquid holding device 16 with an overall stiffness of between about 30 TSU and about 100 TSU.

In the embodiment illustrated in FIG. 8, the access section 28 provides an access opening 29 which has a similar width to the width of the liquid holding device 16 below the access section 28. Alternatively, the access section 28 can provide an access opening 29 which is wider than the liquid holding device 16 below the access section 28.

The width of the liquid holding device 16 can be tapered in the portion 32 below the access opening 29, so as to be continuously narrowed toward the end opposite the access section. In the embodiment illustrated in the FIGS. 1-7, the width of the liquid holding device 16 is continuously tapered below the access opening 29. The wider access section 28 provides easy access of a test device 12. The tapering results in less volume, therefore making it less likely that test liquid 14 will spill out. Tapering also cuts down the cost of raw materials.

It is desirable that the materials used for forming the liquid holding apparatus, at least in the region of the liquid holding device 16, be water proof, non-reactive with all the constituents of the test liquid, and substantially oxygen and water vapor impermeable so the test liquid 14 has at least a thirty day useful life without refrigeration. Preferably any portions of the walls in contact with the test liquid 14 are substantially non-reactive with the test liquid.

For long term stability, preferably the walls resist oxygen and water vapor transmission. Preferably the oxygen and moisture barrier ranges are: OTR (oxygen transmission rate)—<0.02 cc/100 in2/24 hours @73° F. (23° C.), 0% RH; and WVTR (water vapor transmission rate)—<0.16 g/100 in2/24 hours @ 100° F. (38° C.), 90% RH.

In one embodiment, the front wall 24 is made from an extrusion laminate of three materials pressed together. TABLE 1 lists specifications for a typical such three material laminate:

TABLE 1

Material: .48 MIL HIGH BARRIER POLYESTER/.75 MIL EAA/ 1.5 MIL VARIABLE STRENGTH SEALANT FILM In a preferred embodiment, the front wall 24 is made from an extrusion laminate of five materials pressed together. TABLE 2 lists specifications for a typical such five material laminate:

TABLE 2

Material: 0.48 coated polyester (PET)/0.75 low density polyethylene (LDPE)/0.48 high barrier aluminum oxide coated PET/0.75 ethylene acrylic acid(EAA) copolymer clear/1.5 mil variable heat seal strength film (such as a Dupont Surlyn ® material)

Also in a preferred embodiment, the rear wall 26 is made an extrusion laminate of five materials pressed together. TABLE 3 lists specifications for a typical such five material laminate:

TABLE 3

Material: .92 MIL COATED POLYESTER/.75 MIL WHITE LDPE/.285 MIL FOIL/.75 MIL WHITE EAA/1.5 MIL VARIABLE STRENGTH SEALANT FILM The composition of both the front wall 24 and the rear wall 26 can include a variable strength sealant film, such as a variable strength film employing a Surlyn® based resin made by E. I. du Pont de Nemours and Company of Wilmington, Del. Such variable strength seal can be employed to convenient provided desired peel strength lamination by adjusting pressure, temperature and/or dwell time of application. For example, in one embodiment of the invention, desired peel strength for the first lamination 36 can be provided by use of a lamination temperature of about 225° F.-245° F. and the desired peel strength for the second lamination 38 can be provided by use of a lamination temperature of about 245° F.-265° F.

The test liquid 14 can be any of a wide variety of test liquids, depending on the application. In an application where the test device 12 is a urine test strip, the test liquid 14 is test urine control.

FIGS. 10-15 illustrate alternative embodiments wherein the liquid holding device 16 is attached to a backing 18. The backing 18 is attached to at least a portion of the rearward facing surface of the rear wall 26. The backing 18 is stiffer than both the front wall 24 and the rear wall 26.

The backing 18 can be made from a wide variety of materials, such as paper, cardstock, plastic, metal and wood. In a typical embodiment, the backing 18 is made from cardboard, such as 10 point cardboard having the specifications and features set forth below in TABLE 4:

TABLE 4

| A white tag stock suitable for applications which require a stiff facestock with high internal strength. ||
| --- | --- |
| Basis Weight: | 122 lb/ream (500 sheets 24" × 36") |
| Caliper: | 0.010 inches target |
| Tensile: | n/a |
| Tear: | MD 160 grams/sheet, CD 170 grams/sheet |
| Stiffness: | MD 48 gram-cm, CD 24 gram-cm |

The backing 18 can be made with additional stiffness by the application of a stiffening material, such as a stiffening polymer. In a typical embodiment, the stiffening polymer is a clear polypropylene applied to the rearward facing surface of the backing 18. Such clear polypropylene can be a biaxially oriented polypropylene having a total thickness of about 2.0 mils and a film thickness of about 1.2 mils and having the specifications and features set forth below in TABLE 5:

TABLE 5

| | |
|---|---|
| Film: | Biaxially Oriented Polypropylene |
| Total Thickness: | 2.00 mils |
| Film Thickness: | 1.20 mils +/− 5% |
| Adhesive: | Acrylic |

FEATURES

Provides rigidity and extra strength for tag and label applications
Offers enhanced gloss and clarity
Excellent moisture, abrasion, chemical, UV light, and oil resistance

PHYSICAL PROPERTIES

| | | | |
|---|---|---|---|
| Tensile Strength (LBS/IN) | 24 | PSTC*-131 | (ASTM D3759**) |
| Elongation (% At Break) | 160 | PSTC-131 | (ASTM D3759) |
| 180° Peel Adhesion (OZ/IN) | 22 | PSTC-101 | (ASTM D3330***) |

APPLICATION TEMPERATURE

32° F. to 140° F.

OPERATING TEMPERATURE

−10° F. to 200° F. nominal range. Contact your STA representative to determine actual temperature range specific to a particular application.

GOVERNMENT SPECIFICATIONS

Conforms to FDA regulations 21 CFR 175.105 and 21 CFR 177.1520

The backing 18 has a rear face and a forward face facing the liquid holding device 16. The forward face of the backing 18 typically has an adhesive 40 thereon adhering the backing 18 to the liquid holding device 16. A typical adhesive 40 is set forth in TABLE 6:

TABLE 6

An all-purpose cold temperature adhesive featuring good initial tack and ultimate adhesion to a wide variety of substrates.

FDA Compliance: Title 21, Section 175.105 of the Code of Federal Regulations (21 CFR 175.105). Compliance to this regulation permits the use of this adhesive in applications for which the adhesive either (1) is separated from the food by a functional barrier, which will prevent the migration of any of the adhesive components to the food, or (2) has incidental contact with food limited to the trace amount at the seams or the edges of the label.
Type: Emulsion Acrylic
Minimum Application Temperature: −20° F.
Service Temperature Range: −65° F. to +200° F.

The backing layer 18 adds additional stiffness to the liquid holding apparatus 10. A typical overall stiffness of the embodiment illustrated in FIG. 15, for example, is 90 TSU-150 TSU. The backing 18 also provides added strength/rigidity at the neck of the opening that helps prevent the access opening 29 from collapsing when applying pressure to start the peeling process. Yet another advantage of the backing 18 is that it provides added strength at the access opening 29 so that it is easy to slide in a test device 12 because the access opening 29 remains open.

Preferably, the backing 18 extends above the upper section 20 of the liquid holding device 16 to provide a convenient holding tab 42.

In a second aspect, the invention is method of testing a test device 12. The method of testing comprises the step of: a) holding the liquid holding apparatus 10 above the liquid holding device 16; b) opening the access section 28 by peeling the front wall 24 away from the rear wall 26 down to the second lamination 38; and c) inserting the test device 12 into the test liquid 14.

Depending on the application, the test device 12 can be a urine test strip (also termed a "urine dipstick"), a pH probe, a capillary tube, swab, etc. Once adequate separation is achieved, the test device 12 can be introduced into the liquid holding device 16. As the test device 12 is immersed into the test liquid, the fluid level rises—saturating each active portion with test liquid. The tolerances in the liquid holding device 16 provide maximum control as to which active portions 34 are immersed. This is important because some test device manufacturers recommend against flooding the last active portion on the test device 12. Once satisfactory immersion has been achieved, the test device 12 is removed from the liquid holding device 16 and the liquid holding apparatus 10 is discarded.

Exemplary of a commercial test device 12 for urine analysis is Siemens Mutlistix™ 10 SG which tests for glucose, bilirubin, ketone, specific gravity, blood, pH, protein, urobilinogen, nitrite, and leukocytes. The Siemens strip is about 14.6 cm (5¾ inches) long, about 0.5 cm (0.2 inch) wide, about 0.1 cm (0.04 inch) thick at the active portions, with the section of the test device 12 needing contact with the test liquid 14 being about 8.1 cm (4 3/16 inches) long.

In a third aspect, the invention is a method of forming the liquid holding apparatus 10 described above. The method of forming comprising the steps of: a) laminating the front wall 24 to the rear wall 26 except at the access section 28 to form a portion of the liquid holding device 16; b) placing test liquid 14 into that portion of the liquid holding device 16 through the access section 28; c) laminating the front wall 24 to the rear wall 26 at the access section 28; and d) laminating the front wall 24 to the rear wall 26 below the access section 28 with sufficient pressure, temperature and dwell that the seal formed thereby is stronger than the seal at the access section 28.

FIGS. 1-5 and FIGS. 10-13 illustrate the process of forming a first embodiment wherein the lamination in step d) is not continuous to the end of the liquid holding device 16 opposite to the access opening 29.

FIGS. 6-9, 14 and 15 illustrate the process of forming a second embodiment wherein the lamination of step d) is continuous to the end of the liquid holding device 16 opposite to the access section 28. Thus, FIGS. 6-9, 14 and 15 illustrate the lamination of step d) where the lamination of step d) is made to the entire geometry below the access section 28, In FIGS. 6 and 14, the lamination in step d) forms lateral striations. In FIGS. 7, 8 and 15, the lamination in step d) forms vertical striations.

In all cases, the laminations of steps a) and d) can be accomplished using a variable strength sealing layer which provides desired lamination seal strengths by the application of different pressure, temperature and/or dwell conditions.

The invention provides a small portable liquid holding apparatus 10 that is easy to use, inexpensive to manufacture and minimizes spilling accidents.

Although the present invention is described in considerable detail with reference to certain preferred versions thereof, other versions are possible. Therefore the subject claims should not be limited to the preferred versions described.

All the features disclosed in this specification (including any accompanying claims, abstract, and drawings) may be replaced by alternative features serving the same, equivalent or similar purpose, unless each feature disclosed is one example only of a generic series of equivalent or similar features.

What is claimed is:

1. A testing apparatus for an elongated test strip comprising:
   a) a front wall and a rear wall sealed together at their peripheral edges;
   b) a single elongated space between the front and rear wall and having peripheral edges inwardly from the peripheral edges of the wall, the elongated space having a top portion;
   c) test liquid without any test strip in the elongated space, wherein the test liquid is in an amount of no more than about 80% of the total capacity of the elongated space;
   d) an access section only at the top portion of the elongated space for insertion of the test strip into the test liquid, the access section having a lower stop-peel border;
   e) a peelable lamination formed by heat welding the front and rear walls together, the peelable lamination having a first peel strength and peelable by finger strength so that the access section is accessible for one-time use by peeling the front wall from the rear wall by finger strength; and
   f) a stop-peel lamination formed by heat welding the front and rear walls together, the stop-peel lamination being below the peelable lamination and proximate to the elongated space and extending to the lower stop-peel border of the access section to provide a permanent seal, the stop-peel lamination having a second peel strength greater than the first peel strength so that the finger strength for peeling the peelable lamination does not peel the stop-peel lamination for preventing leakage of test liquid from the elongated space, the stop-peel lamination providing a stiffness of at least about 15 TSU, wherein the stop-peel lamination comprises multiple vertical striations extending along the peripheral edges of the elongated space and the single elongated space is at least 90 mm in length as measured from the access section.

2. The testing apparatus of claim 1, wherein the vertical striations are disposed along the entire length of the testing apparatus, except the upper access section.

3. The testing apparatus of claim 1, wherein the vertical striations are disposed along the entire length of the testing apparatus below the lower stop-peel border of the access section.

4. The testing apparatus of claim 1, wherein the vertical striations are disposed below the access section.

5. The testing apparatus of claim 1 wherein the front wall is made from an extrusion laminate of five materials comprising coated polyester, low density polyethylene, high barrier aluminum oxide coated polyester, ethylene acrylic acid copolymer and a variable heat seal strength film, and the rear wall is made from an extrusion laminate of five materials comprising coated polyester, low density polyethylene, foil, ethylene acrylic acid and a variable strength sealant film.

6. The testing apparatus of claim 1, wherein the access section comprises an access opening that has a width that is larger than a width of the elongated space.

7. The testing apparatus of claim 1 wherein the elongated space is sufficiently long that a test strip which is 146 mm (5¾ inches) long, 5 mm (0.2 inch) wide, and 1 mm (0.04 inch) thick and having active portions, with the section having the active portions being 81 mm (4³⁄₁₆ inches) long, can be dipped into the elongated space with all of the active portions in contact with test liquid.

8. The apparatus of claim 1, wherein a testing strip can be dipped into the test liquid without any test liquid leaking out of the single elongated space.

9. A testing apparatus for an elongated test strip comprising:
   a) a front wall and a rear wall sealed together at their peripheral edges;
   b) a single elongated space between the front and rear wall and having peripheral edges inwardly from the peripheral edges of the wall, the elongated space having a top portion;
   c) test liquid without any test strip in the elongated space;
   d) an access section only at the top portion of the elongated space for insertion of the test strip into the test liquid, the access section having a lower stop-peel border;
   e) a peelable lamination formed by heat welding the front and rear walls together, the peelable lamination having a first peel strength and peelable by finger strength so that the access section is accessible for one-time use by peeling the front wall from the rear wall by finger strength; and
   f) a stop-peel lamination formed by heat welding the front and rear walls together, the stop-peel lamination being below the peelable lamination and proximate to the elongated space and extending to the lower stop-peel border of the access section to provide a permanent seal, the stop-peel lamination having a second peel strength greater than the first peel strength so that the finger strength for peeling the peelable lamination does not peel the stop-peel lamination for preventing leakage of test liquid from the elongated space, the stop-peel lamination providing a stiffness of at least about 15 TSU.

10. The testing apparatus of claim 9, wherein the stop-peel lamination comprises multiple vertical striations.

11. The testing apparatus of claim 10, wherein vertical striations extend along the peripheral edges of the elongated space.

12. The testing apparatus of claim 10, wherein the vertical striations are disposed along the entire length of the testing apparatus, except the upper access section.

13. The testing apparatus of claim 10, wherein the vertical striations are disposed along the entire length of the testing apparatus below the lower stop-peel border of the access section.

14. The testing apparatus of claim 10, wherein the vertical striations are disposed below the access section.

15. The testing apparatus of claim 9, wherein the testing apparatus contains test liquid in an amount of no more than about 80% of the total capacity of the elongated space.

16. The testing apparatus of claim 9, wherein the front wall is made from an extrusion laminate of five materials comprising coated polyester, low density polyethylene, high barrier aluminum oxide coated polyester, ethylene acrylic acid copolymer and a variable heat seal strength film, and the rear wall is made from an extrusion laminate of five materials comprising coated polyester, low density polyethylene, foil, ethylene acrylic acid and a variable strength sealant film.

17. The testing apparatus of claim 9, wherein the access section comprises an access opening that has a width that is larger than a width of the elongated space.

18. The testing apparatus of claim 9, wherein the elongated space is sufficiently long that a test strip which is 146 mm (5¾ inches) long, 5 mm (0.2 inch) wide, and 1 mm (0.04 inch) thick and having active portions, with the section having the active portions being 81 mm (4³⁄₁₆ inches) long, can be dipped into the elongated space with all of the active portions in contact with test liquid, and, wherein the elongated space is at least 90 mm in length as measured from the access section to the bottom of the testing apparatus.

19. The apparatus of claim 9, wherein the test liquid is no more than about 80% of the total capacity of the single elongated space such that a testing strip can be dipped therein without any test liquid leaking out of the single elongated space.

20. A method of testing an elongated test strip comprising the steps of:
   a) selecting a testing apparatus for the elongated test strip comprising:
      i) a front wall and a rear wall sealed together at their peripheral edges;
      ii) a single elongated space between the front and rear wall and having peripheral edges inwardly from the peripheral edges of the wall, the elongated space having a top portion;
      iii) test liquid without any test strip in the elongated space;
      iv) an access section only at the top portion of the elongated space for insertion of the test strip into the test liquid, the access section having a lower stop-peel border;
      v) a peelable lamination formed by heat welding the front and rear walls together, the peelable lamination having a first peel strength and peelable by finger strength so that the access section is accessible for one-time use by peeling the front wall from the rear wall by finger strength; and
      vi) a stop-peel lamination formed by heat welding the front and rear walls together, the stop-peel lamination being below the peelable lamination and proximate to the elongated space and extending to the lower border of the access section to provide a permanent seal, the stop-peel lamination having a second peel strength greater than the first peel strength so that the finger strength for peeling the peelable lamination does not peel the stop-peel lamination for preventing leakage of test liquid from the elongated space, the stop-peel lamination providing a stiffness of at least about 15 TSU;
   b) peeling the front and rear walls apart at the access section up to the lower stop-peel border, leaving the stop-peel lamination permanently intact; and
   c) while holding the testing apparatus, placing the test strip into the test liquid without leaking any test liquid out of the elongated space.

21. A testing apparatus for an elongated test strip comprising:
   a) a front wall and a rear wall sealed together at their peripheral edges;
   b) a single elongated space between the front and rear wall and having peripheral edges inwardly from the peripheral edges of the wall, the elongated space having a top portion;
   c) test liquid without any test strip in the elongated space, wherein the test liquid is in an amount of no more than about 80% of the total capacity of the elongated space;
   d) an access section only at the top portion of the elongated space for insertion of the test strip into the test liquid, the access section having a lower stop-peel border;
   e) a peelable lamination formed by heat welding the front and rear walls together, the peelable lamination having a first peel strength and peelable by finger strength so that the access section is accessible for one-time use by peeling the front wall from the rear wall by finger strength; and
   f) a stop-peel lamination formed by heat welding the front and rear walls together, the stop-peel lamination being below the peelable lamination and proximate to the elongated space and extending to the lower stop-peel border of the access section to provide a permanent seal, the stop-peel lamination having a second peel strength greater than the first peel strength so that the finger strength for peeling the peelable lamination does not peel the stop-peel lamination for preventing leakage of test liquid from the elongated space, the stop-peel lamination providing a stiffness of at least about 15 TSU, wherein the stop-peel lamination comprises multiple striations along the peripheral edges of the elongated space.

22. The apparatus of claim 9 wherein the test liquid is for testing a urine test strip.

23. The apparatus of claim 21, wherein a testing strip can be dipped into the test liquid without any test liquid leaking out of the single elongated space.

* * * * *